United States Patent [19]

Simpson

[11] 4,378,369
[45] Mar. 29, 1983

[54] ESTERS OF 2,5-ANHYDRO-D-MANNITOL

[75] Inventor: Ronald Simpson, Mendham, N.J.

[73] Assignee: Sandoz, Inc., East Hanover, N.J.

[21] Appl. No.: 308,269

[22] Filed: Oct. 5, 1981

[51] Int. Cl.³ .................... A61K 31/34; C07D 307/60
[52] U.S. Cl. .................................... 424/285; 549/478
[58] Field of Search .................... 260/347.4; 536/119; 424/180, 285

[56] References Cited

U.S. PATENT DOCUMENTS 3,096,324 7/1963 Goins et al. .................... 536/119
3,956,278 5/1976 Prey .................................. 536/119

OTHER PUBLICATIONS

Stevens et al., Fed. Proc., 40, No. 3, (1981), p. 842.
Koernor et al., Chemical Abstracts, vol. 88, (1978), 105668u.
Bera et al., J. Chem. Soc., (1956), pp. 4531–4535.

Primary Examiner—Richard Raymond
Attorney, Agent, or Firm—Gerald D. Sharkin; Robert S. Honor; Joseph J. Borovian

[57] ABSTRACT

Agents for lowering glucose levels in blood having the formula:

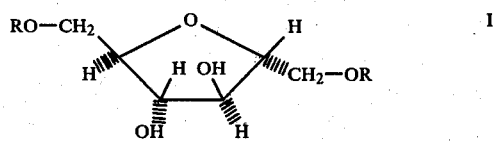

wherein each R, independently, is hydrogen, $C_{1-6}$ alkyl-carbonyl or a group of the formula

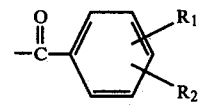

where
$R_1$ is hydrogen, $C_{1-4}$ alkyl, $C_{1-4}$-alkoxy, halo or trifluoromethyl, and
$R_2$ is hydrogen, $C_{1-3}$ alkyl, $C_{1-3}$ alkoxy or halo, with the proviso that when one R is hydrogen, the other R is not hydrogen.

11 Claims, No Drawings

ESTERS OF 2,5-ANHYDRO-D-MANNITOL

The present invention relates to certain mono- and diesters of 2,5-anhydro-D-mannitol and to their use as hypoglycemic agents. The invention also relates to pharmaceutical compositions containing the above compounds as an active ingredient thereof and to the method of using such compositions for lowering blood glucose levels in, e.g., the treatment of diabetes.

The compound, 2,5-anhydro-D-mannitol, is known and may be prepared by methods described in the literature, e.g., by the method described by B. C. Bera, A. B. Foster and M. Stacey in J. Chem. Soc., pp. 4531–4535 (1956).

In addition, the compounds 2,5-anhydro-D-glucitol (sorbitol), 2,5-anhydro-1,6-O-benzoyl-D-glucitol, 1,3,4,6-tetra-O-acetyl-2,5-anhydro-D-glucitol, 3,4-di-O-acetyl-2,5-anhydro-1,6-di-O-benzoyl-D-glucitol and tetra-O-acetyl-2,5-anhydro-D-mannitol are described by Koerner, Jr., et al in Carbohydrate Res. 59(2) 403–416 (1977); however, to my knowledge, no pharmacological activity has been heretofore associated with any of these compounds.

The present invention involves the novel compounds of formula I:

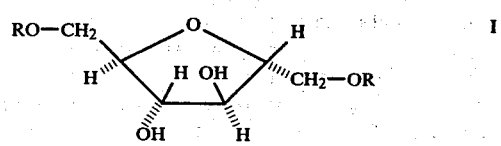

wherein each R, independently, is hydrogen, $C_{1-6}$ alkylcarbonyl or a group of the formula

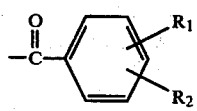

where
$R_1$ is hydrogen, $C_{1-4}$ alkyl, $C_{1-4}$-alkoxy, halo or trifluoromethyl, and
$R_2$ is hydrogen, $C_{1-3}$ alkyl, $C_{1-3}$ alkoxy or halo, with the proviso that when one R is hydrogen, the other R is not hydrogen.

Included among the class of compounds of formula I are the compounds of subclass Ia:

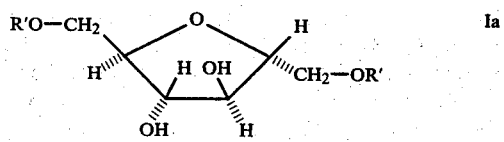

where each R' is a group of the formula

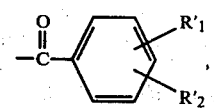

where $R_1'$ and $R_2'$ have the same significances as $R_1$ and $R_2$ defined above. Preferred compounds of subclass Ia are compounds wherein $R_1'$ is hydrogen, $C_{1-4}$ alkyl, $C_{1-4}$ alkoxy, chloro, fluoro or trifluoromethyl and $R_2'$ is hydrogen, $C_{1-3}$ alkyl, $C_{1-3}$ alkoxy, chloro or fluoro. The more preferred compounds of subclass Ia are compounds wherein $R_1'$ is hydrogen, methyl, ethyl, methoxy, ethoxy, chloro, fluoro or trifluoromethyl and $R_2'$ is hydrogen, methyl, ethyl, methoxy, ethoxy, chloro or fluoro. The most preferred compound of subclass Ia is 2,5-anhydro-1,6-di-O-benzoyl-D-mannitol.

Also included among the class of compounds of formula I are the compounds of subclass Ib:

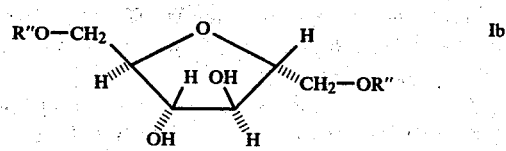

where each R" is $C_{1-6}$ alkylcarbonyl. Preferred compounds of subclass Ib are compounds wherein R" is $C_{1-4}$ alkylcarbonyl, more preferably $C_1$ or $C_2$ alkylcarbonyl. The most preferred compound of subclass Ib is 1,6-di-O-acetyl-2,5-anhydro-D-mannitol.

Further representative of the class of compounds of formula I are the compounds of subclass Ic:

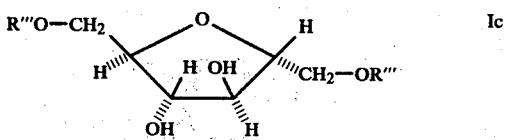

where each R'" is $C_{1-6}$ alkylcarbonyl or a group of the formula

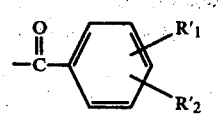

where $R_1'$ and $R_2'$ have the same significances as $R_1$ and $R_2$ defined above, with the proviso that one R'" substituent is $C_{1-6}$ alkylcarbonyl and the other R'" substituent is a group of the formula

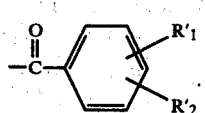

Preferred compounds of subclass Ic are compounds wherein each $R_1'''$ is $C_{1-4}$ alkylcarbonyl or a group of the formula

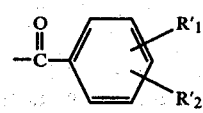

where $R_1'$ is hydrogen, $C_{1-4}$ alkyl, $C_{1-4}$ alkoxy, chloro, fluoro or trifluoromethyl and $R_2'$ is hydrogen, $C_{1-3}$ alkyl, $C_{1-3}$ alkoxy, chloro or fluoro and wherein the above proviso applies. The more preferred compounds of subclass Ic are compounds wherein each R'" is $C_1$ or $C_2$ alkylcarbonyl or a group of the formula

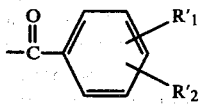

where $R_1'$ is hydrogen, methyl, ethyl, methoxy, ethoxy, chloro, fluoro or trifluoromethyl and $R_2'$ is hydrogen, methyl, ethyl, methoxy, ethoxy, chloro or fluoro and wherein the above proviso applies. The most preferred compound of subclass Ic is 1-O-acetyl-2,5-anhydro-6-O-benzoyl-D-mannitol.

Also representative of the class of compounds of formula I are the compounds of subclass Id:

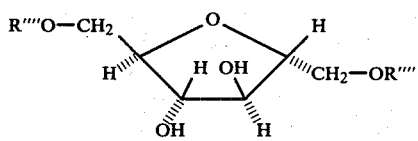

where one R"" is hydrogen and the other R"" is $C_{1-6}$ alkylcarbonyl or a group of the formula

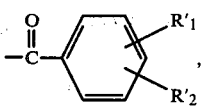

where $R_1'$ and $R_2'$ have the same significances as $R_1$ and $R_2$ defined above. Preferred compounds of subclass Id are compounds wherein one R"" is hydrogen and the other R"" is $C_{1-4}$ alkylcarbonyl or a group of the formula

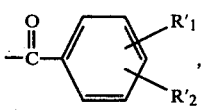

where $R_1'$ is hydrogen, $C_{1-4}$ alkyl, $C_{1-4}$ alkoxy, chloro, fluoro or trifluoromethyl and $R_2'$ is hydrogen, $C_{1-3}$ alkyl, $C_{1-3}$ alkoxy, chloro or fluoro. The more preferred compounds of subclass Id are compounds wherein one R"" is hydrogen and the other R"" is $C_1$ or $C_2$ alkylcarbonyl or a group of the formula

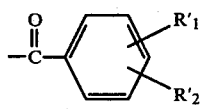

where $R_1'$ is hydrogen, methyl, ethyl, methoxy, ethoxy, chloro, fluoro or trifluoromethyl and $R_2'$ is hydrogen, methyl, ethyl, methoxy, ethoxy, chloro or fluoro. The most preferred compounds of subclass Id are 2,5-anhydro-6-O-benzoyl-D-mannitol and 6-O-acetyl-2,5-anhydro-D-mannitol.

The compounds of subclass Ia may be prepared by aroylation (process (a)) of the compound of formula II:

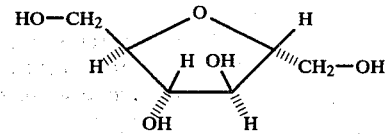

with an aroylating agent, i.e., a compound of formula III:

$R_3$—X          III where $R_3$ has the same significance as R' defined above, and X is chloro, bromo or a group

where $R_3$ is as defined above.

The aroylation of a compound of formula II may be carried out by procedures conventionally employed for the aroylation of alcohols. Suitable aroylating agents (III) include optionally substituted benzoyl halides and optionally substituted benzoic anhydrides. The aroylation is conducted in the presence of an organic base, e.g., pyridine, triethylamine, etc. In addition, the aroylation is suitably carried out in the presence of an inert, organic solvent, e.g., a cyclic ether such as tetrahydrofuran, or excess aroylating agent may serve as the solvent. The aroylation is conveniently carried out at temperatures of between $-25°$ C. and $80°$ C., preferably between $-10°$ C. and $65°$ C., and in a molar ratio of aroylating agent to compound of formula II of at least 2:1.

The compounds of subclass Ib may be prepared by alkanoylation (process (b)) of a compound of formula II, as defined above, with an alkanoylating agent, i.e., a compound of formula IV:

$R_4$—Y          IV where $R_4$ is $C_{2-7}$ alkanoyl, and Y is chloro, bromo or a group

where $R_4$ is as defined above.

The alkanoylation of a compound of formula II may be carried out by conventional techniques. The alkanoylation, thus, may be effected by processes known per se for the alkanoylation of alcohols. Suitable alkanoylating agents (IV) include acyl halides and acid anhydrides. In carrying out the alkanoylation, inert solvent may be employed or excess alkanoylating agent may serve as solvent. In addition, an acid binding agent, e.g., pyridine, may be employed. The alkanoylation is conveniently carried out at temperatures of between $-30°$ C. and $100°$ C., preferably between $0°$ C. and $100°$ C., and in a molar ratio of alkanoylating agent to compound of formula II of at least 2:1.

The compounds of subclass Ic may be prepared by a two-step reaction wherein a compound of formula II is aroylated (process (a)) by reaction with a compound of formula III, as defined above, in a molar ratio of 1:1, to produce an intermediate compound of formula V:

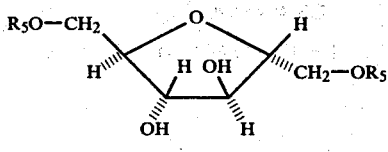

where one $R_5$ is hydrogen and the other $R_5$ is a group of the formula

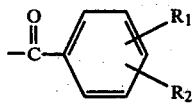

where $R_1$ and $R_2$ are as defined above. The second step involves the alkanoylation (process (b)) of a compound of formula V, as defined above, by reaction with a compound of formula IV, as defined above, in a molar ratio of 1:1.

Conversely, the compounds of subclass Ic may be prepared by a two-step reaction wherein a compound of formula II is alkanoylated (process (b)) by reaction with a compound of formula IV, as defined above, in a molar ratio of 1:1, to produce an intermediate compound of formula VI:

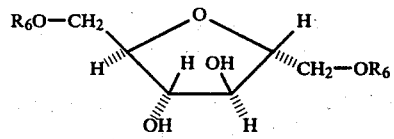

where one $R_6$ is hydrogen and the other $R_6$ is $C_{1-6}$ alkylcarbonyl. The second step involves the aroylation (process (a)) of a compound of formula VI, as defined above, by reaction with a compound of formula III, as defined above, in a molar ratio of 1:1.

The compounds of subclass Id where one $R''''$ is hydrogen and the other $R''''$ is $C_{1-6}$ alkylcarbonyl may be prepared by the mono-alkanoylation (process (c)) of a compound of formula II, as defined above, by reaction with a compound of formula IV, as defined above. The mono-alkanoylation is carried out essentially as the alkanoylation described above, save for the fact that the molar ratio of alkanoylating agent to compound of formula II is 1:1.

The compounds of subclass Id where one $R''''$ is hydrogen and the other $R''''$ is a group of the formula

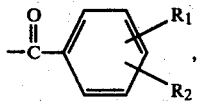

where $R_1$ and $R_2$ are as defined above, may be prepared by the mono-aroylation (process (d)) of a compound of formula II, as defined above, by reaction with a compound of formula III, as defined above. The mono-aroylation is carried out essentially as the aroylation described above, save for the fact that the molar ratio of aroylating agent to compound of formula II is 1:1.

The products of the above-described reactions may be recovered and refined in conventional manner, e.g., by crystallization, distillation or chromatographic techniques, such as eluting from a chromatographic column or separating on a silica layer.

The compound of formula II is known, whereas the compounds of formulae III and IV are either known and obtained by methods described in the literature, or where not known, may be obtained by methods analogous to those described in the literature.

The compounds of formula I are useful in lowering glucose levels in blood in, e.g., the treatment of diabetes, as indicated in 6 to 8 week old male Royal Hart mice weighing 28 to 35 grams which are fasted in groups of 5 to 7 for 16 hours and then are given an initial dose of 50 to 400 milligrams per kilogram of animal body weight of the compound orally. Two hours after the test compound is administered, the mice are anesthetized with 85 milligrams per kilogram of animal body weight of sodium hexobarbital and five minutes later blood is collected via cardiac puncture. The blood samples are placed in an autoanalyzer cup containing 0.025 milliliters of heparin (1,000 units per milliliter); and the samples are capped, shaken and stored in ice. The glucose level is determined by the autoanalyzer potassium ferric cyanide N-2b method and these glucose levels are then compared with the glucose levels of the control group which receives orally 0.5% carboxymethyl cellulose and is run concurrently.

The compounds of formula I may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The composition for oral use may contain one of more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The effective amount of active ingredient employed for lowering blood glucose levels in, e.g., the treatment of diabetes, may vary depending on the particular compound employed, the mode of administration and the severity of the condition being treated. However, in general, satisfactory results in, e.g., the treatment of diabetes, are obtained when a compound of formula I is administered at a daily dosage of from about 5 milligrams to about 200 milligrams per kilogram of animal body weight, preferably given orally and in divided doses two to four times a day, or in sustained release form. For most large mammals, the total daily dosage is from about 400 milligrams to about 4000 milligrams. Unit dosage forms suitable for internal use comprise from about 75 milligrams to about 2000 milligrams, more usually 75 to 1000 milligrams, of the active compound in intimate admixture with a solid or liquid, pharmaceutically acceptable carrier.

Tablets and capsules containing the ingredients indicated below may be prepared by conventional techniques and are useful in treating diabetes at a dose of one tablet or capsule, 2 to 4 times a day.

| Ingredients | Weight (mg.) tablet | capsule |
|---|---|---|
| 2,5-anhydro-1,6-di-O—benzoyl-D-mannitol | 100 | 100 |
| tragacanth | 10 | — |
| lactose | 247.5 | 300 |
| corn starch | 25 | — |
| talcum | 15 | — |
| magnesium stearate | 2.5 | — |
| Total | 400.0 | 400.0 |

The following pharmaceutical compositions are formulated with the indicated amount of active ingredient using conventional techniques. The injectable suspension and the oral suspension represent formulations useful as unit doses and may be administered in the treatment of diabetes. The injectable suspension is suitable for administration once or twice a day whereas the oral liquid suspension is suitably administered 2 to 4 times per day.

| Ingredients | Weight (mg.) sterile injectable suspension | oral liquid suspension |
|---|---|---|
| 2,5-anhydro-1,6-di-O—benzoyl-D-mannitol | 200 | 100 |
| sodium carboxymethylcellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g. Tween 80), U.S.P. | — | 5 |
| sorbitol solution, 70%, U.S.P. | — | 2,500 |
| buffer agent to adjust pH for desired stability | q.s. | q.s. |
| water | for injection, q.s. to 1 ml. | q.s. to 5 ml |

The preferred pharmaceutical compositions from the standpoint of preparation and ease of administration are solid compositions, particularly liquid or hard filled capsules and tablets containing from about 100 to 200 milligrams of the active ingredient.

The following examples are merely illustrative of representative compounds encompassed by this invention and their synthesis.

EXAMPLE 1

2,5-anhydro-1,6-di-O-benzoyl-D-mannitol

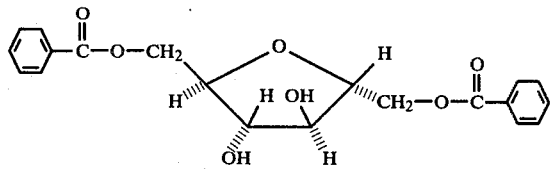

(a) 0.45 g. (0.36 ml.; 3.15 mmol) of benzoyl chloride was added to a solution of 0.16 g. (1 mmol.) of 2,5-anhydro-D-mannitol in 3 ml. of pyridine and the reaction mixture was stirred at 50° C. for 4 hrs. The reaction mixture was allowed to cool and was evaporated under high vacuum. The residue was dried under high vacuum and partitioned between chloroform and water. The aqueous phase was extracted twice with chloroform and the three chloroform phases were combined, dried over anhydrous magnesium sulfate and evaporated at reduced pressure to an oil. The oil was filtered through 5 ml. of silica gel using chloroform and 5% methanol/chloroform to elute the dibenzoate compound. The fractions containing the product as indicated by thin layer chromatography were combined and evaporated at reduced pressure, and the residue was dried under high vacuum, crystallized by scratching and triturated with pentane to obtain the white crystalline product (0.16 g.), m.p. 100°–102° C.

$ED_{25} - \simeq 150$ mg./kg.

(b) To a suspension of 0.82 g. (0.5 mmol) of 2,5-anhydro-D-mannitol in 5 ml. of tetrahydrofuran, is added successively, 0.11 g. (0.16 ml.; 1.1 mmol) of triethylamine and 0.155 g. (0.13 ml.; 1.1 mmol) of benzoyl chloride. The reaction mixture is then stirred for 2 hrs. at room temperature, after which time it is refluxed for 3 hrs., allowed to cool and evaporated under high vacuum. The residue was dried under high vacuum and partitioned between chloroform and water. The aqueous phase was extracted twice with chloroform and the three chloroform phases were combined, dried over anhydrous magnesium sulfate and evaporated at reduced pressure to an oil. The oil was filtered through 50 ml. of silica gel using chloroform and 5% methanol/chloroform to elute the dibenzoate compound. The fractions containing the product as indicated by thin layer chromatography were combined and evaporated at reduced pressure, and the residue was dried under high vacuum, crystallized by scratching and triturated with pentane to obtain the white crystalline product (1.67 g.).

EXAMPLE 2

Following the procedure of Example 1(b), but employing appropriate starting materials in approximately equivalent amounts, the compound 2,5-anhydro-1,6-di-O-toluoyl-D-mannitol, m.p. 87°–89° C., was prepared.

EXAMPLE 3

1,6-di-O-acetyl-2,5-anhydro-D-mannitol

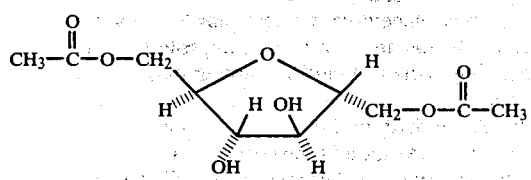

A solution of 1.64 g. (10 mmol.) of 2,5-anhydro-D-mannitol in pyridine is cooled to −10° C., treated with 2.1 g. (20 mmol.) of acetic anhydride and allowed to come to room temperature over a period of 2 hours. After 15 hours at room temperature, the solvent is removed in vacuo to yield an oil which is purified by chromatography on silica gel to yield the title compound.

EXAMPLE 4

2,5-anhydro-6-O-benzoyl-D-mannitol

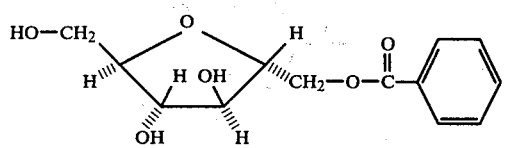

7.9 g. (6.5 ml., 56.3 mmol.) of benzoyl chloride and 5.7 g. (8.02 ml., 56.3 mmol.) of triethylamine were added to a suspension of 8.4 g. (51.2 mmol.) of 2,5-anhydro-D-mannitol in 100 ml. of tetrahydrofuran. The reaction mixture was refluxed for 5 hrs., allowed to cool to room temperature and evaporated at room temperature and 200 ml. of chloroform is added to the residue. The solids were removed by filtration and washed with chloroform and the chloroform filtrate and washings were combined and evaporated at reduced pressure. The residue was filtered through 200 ml. of silica gel utilizing chloroform and 5% methanol/chloroform to elute the dibenzoate and 5% methanol/chloroform and 10% methanol/chloroform to elute the monobenzoate. The fractions containing the monobenzoate (as indicated by thin layer chromatography) were combined and evaporated at reduced pressure to an uncrystallizable, very thick oil. The oil was distilled in a Kugelrohr apparatus at 135°–145° C. and 40μ. to obtain a thick, pale yellow oil (2.50 g.) $[\alpha]_D = +46.191°$ (methanol). −27% (200 mg./kg.)

EXAMPLE 5

1-O-acetyl-2,5-anhydro-6-O-benzoyl-D-mannitol

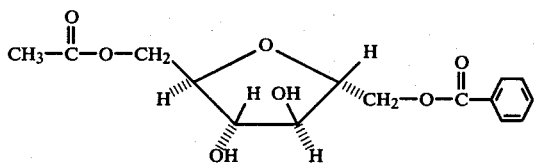

The monobenzoate of Example (4) above is dissolved in 30 ml. of pyridine and the resulting solution is cooled to −10° C. To the cooled solution is added 1 g. of acetic anhydride and the reaction mixture is allowed to come to room temperature over a period of 2 hours. After 15 hours at room temperature, the solvent is removed in vacuo to obtain an oil which is purified by chromatography on silica gel to yield the title compound.

EXAMPLE 6

Following the procedure of Example 3, but employing one half the amount of acetic anhydride, the compound, 6-O-acetyl-2,5-anhydro-D-mannitol, is prepared.

What is claimed is:

1. A compound of formula I:

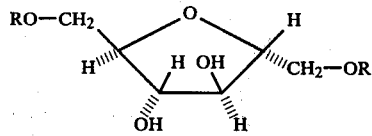

wherein each R, independently, is hydrogen, $C_{1-6}$ alkylcarbonyl or a group of the formula

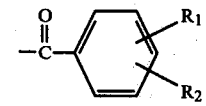

where
$R_1$ is hydrogen, $C_{1-4}$ alkyl, $C_{1-4}$-alkoxy, halo or trifluoromethyl, and
$R_2$ is hydrogen, $C_{1-3}$ alkyl, $C_{1-3}$ alkoxy or halo, with the proviso that when one R is hydrogen, the other R is not hydrogen.

2. A compound according to claim 1 of formula Ia:

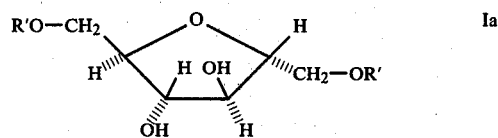

wherein each R′ is a group of the formula

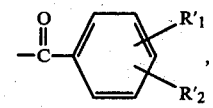

where $R_1′$ and $R_2′$ have the same significances as $R_1$ and $R_2$ defined in claim 1.

3. The compound according to claim 2 which is 2,5-anhydro-1,6-di-O-benzoyl-D-mannitol.

4. The compound according to claim 2 which is 2,5-anhydro-1,6-di-O-toluoyl-D-mannitol.

5. A compound according to claim 1 of formula Ib:

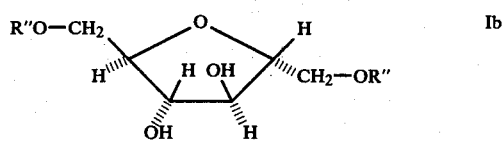

wherein each R″ is $C_{1-6}$ alkylcarbonyl.

6. A compound according to claim 1 of formula Ic:

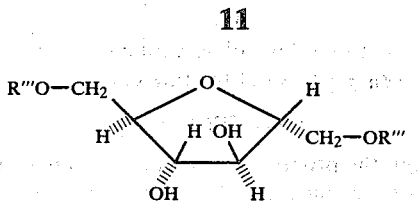

wherein each R''' is $C_{1-6}$ alkylcarbonyl or a group of the formula

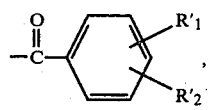

where $R_1'$ and $R_2'$ have the same significances as $R_1$ and $R_2$ defined in claim 1, with the proviso that one R''' substituent is $C_{1-6}$ alkylcarbonyl and the other R''' substituent is a group of the formula

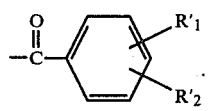

7. A compound according to claim 1 of formula Id:

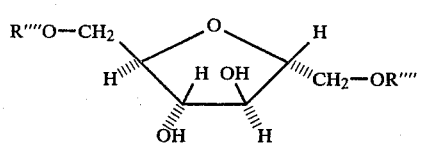

wherein one R'''' is hydrogen and the other R'''' is $C_{1-6}$ alkylcarbonyl or a group of the formula

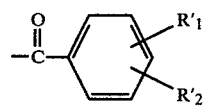

where $R_1'$ and $R_2'$ have the same significances as $R_1$ and $R_2$ defined in claim 1.

8. The compound according to claim 7 which is 2,5-anhydro-6-O-benzoyl-D-mannitol.

9. A pharmaceutical composition for lowering blood glucose levels in mammals comprising a compound according to claim 1, and a pharmaceutically acceptable carrier.

10. A method of lowering glucose levels in blood plasma comprising administering to a mammal in need of such treatment a therapeutically effective amount of a compound of formula I:

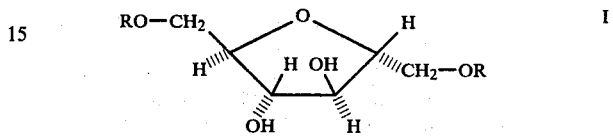

wherein each R, independently, is hydrogen, $C_{1-6}$ alkylcarbonyl or a group of the formula

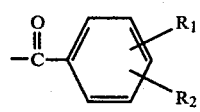

where
$R_1$ is hydrogen, $C_{1-4}$ alkyl, $C_{1-4}$-alkoxy, halo or trifluoromethyl, and
$R_2$ is hydrogen, $C_{1-3}$ alkyl, $C_{1-3}$ alkoxy or halo, with the proviso that when one R is hydrogen, the other R is not hydrogen,
said therapeutically effective amount being an amount effective for the lowering of blood glucose levels.

11. A method of treating diabetes by lowering the glucose levels in blood plasma according to claim 10 comprising administering to a diabetic host a therapeutically effective amount of a compound of formula I as defined in claim 12, said therapeutically effective amount being an amount effective for the treatment of diabetes.

* * * * *